US011975192B2

(12) United States Patent
Chen

(10) Patent No.: US 11,975,192 B2
(45) Date of Patent: May 7, 2024

(54) INNER EAR APPARATUS

(71) Applicant: Taiting Chen, Taipei (TW)

(72) Inventor: Taiting Chen, Taipei (TW)

( * ) Notice: Subject to any disclaimer, the term of this patent is extended or adjusted under 35 U.S.C. 154(b) by 84 days.

(21) Appl. No.: 17/367,125

(22) Filed: Jul. 2, 2021

(65) Prior Publication Data

US 2021/0330976 A1 Oct. 28, 2021

Related U.S. Application Data

(62) Division of application No. 16/273,268, filed on Feb. 12, 2019, now abandoned.

(60) Provisional application No. 62/629,158, filed on Feb. 12, 2018.

(51) Int. Cl.
*A61N 1/36* (2006.01)
*H04R 25/00* (2006.01)

(52) U.S. Cl.
CPC ......... *A61N 1/36038* (2017.08); *H04R 25/45* (2013.01); *H04R 25/502* (2013.01); *H04R 25/554* (2013.01)

(58) Field of Classification Search
CPC .................................. A61N 1/36038
See application file for complete search history.

(56) References Cited

U.S. PATENT DOCUMENTS

| | | | | |
|---|---|---|---|---|
| 5,776,179 A * | 7/1998 | Ren | ...................... | A61B 5/0093 607/57 |
| 6,295,472 B1 * | 9/2001 | Rubinstein | ............. | H04R 25/75 607/55 |
| 6,754,537 B1 * | 6/2004 | Harrison | ............ | A61N 1/36038 607/57 |
| 7,856,275 B1 * | 12/2010 | Paul | .................... | A61N 1/36014 607/55 |
| 8,233,651 B1 * | 7/2012 | Haller | .................. | H04R 25/456 381/328 |
| 8,265,765 B2 * | 9/2012 | Nicolai | .................. | H04R 25/70 607/57 |
| 8,437,859 B1 * | 5/2013 | Haller | ................ | A61N 1/36038 607/55 |
| 8,699,734 B1 * | 4/2014 | Haller | ................ | A61N 1/36038 381/328 |
| 9,320,898 B2 * | 4/2016 | Downing | ............... | H04R 25/02 |
| 10,492,010 B2 * | 11/2019 | Rucker | ................ | H04R 25/606 |
| 2002/0091423 A1 * | 7/2002 | Rubinstein | ............. | H04R 25/75 607/55 |

(Continued)

*Primary Examiner* — Eric D. Bertram
(74) *Attorney, Agent, or Firm* — Chun-Ming Shih; LANWAY IPR SERVICES

(57) ABSTRACT

A hearing-aid apparatus includes an audio collector, an audio processor, a speaker and an inner-ear implant device. The audio collector collects audio information. The speaker generates a sound wave by reference to the audio information. The sound wave is transmitted to an inner ear of a user. The inner-ear implant device is implanted aside a round window of the user for generating an electrical signal encoded by the audio processor based on the audio information to stimulate high frequency auditory nerve cells of the user with an electrode of the inner-ear implant device. The audio wave sent to the inner ear of and the electrical signal stimulating the auditory nerve cells together form an integrated auditory recognition corresponding to the audio information.

18 Claims, 3 Drawing Sheets

(56) References Cited

U.S. PATENT DOCUMENTS

| | | | |
|---|---|---|---|
| 2007/0213787 A1* | 9/2007 | Kuzma | A61N 1/361 |
| | | | 607/55 |
| 2012/0095527 A1* | 4/2012 | Vardi | A61N 1/0541 |
| | | | 607/57 |
| 2018/0304077 A1* | 10/2018 | Lee | A61N 1/37229 |
| 2019/0167985 A1* | 6/2019 | Carlson | A61N 1/361 |

* cited by examiner

INNER EAR APPARATUS

RELATED APPLICATION

This application is a continued application of application Ser. No. 16/273,268, which claims priority of a provisional application No. 62/629,158.

FIELD OF THE INVENTION

The present invention is related to a hearing-aid device and more particularly related to a hearing-aid device with inner ear implant component.

BACKGROUND

There are various cochlear implant devices, usually including a flexible band with multiple electrodes to stimulate different positions of patient's auditory nerve cells distributed in the cochlear of the patient, so as to generate low frequency, middle frequency and high frequency band of sound recognition in patient's brain.

Such cochlear implant devices need complicated and risky surgery including to open a hole in cranial bone of the patient and inserted the cochlear implant devices into the cochlear of the patient. This is amazing and great to save thousands of patients to hear again or firstly to hear sounds. But, they are expensive and risky and until now, there are many patients who need such surgery awaiting resources to do so.

On the other hand, when human life is longer and longer, more and more people face hearing problems. Most of them can hear clearly when they are young, but when ages grow, they gradually lose their hearing ability.

Hearing-aid devices are common, therefore, in daily life. There are many elder people wearing hearing-aid devices as an auxiliary tool to help them handle daily life. Common hearing-aid devices have simple structures, 95% made by five major manufacturers around the world. Such hearing-aid devices have microphones, a processor to amplifies the sounds collected by the microphones and a speaker near the ear to speak the amplified sounds loudly.

These devices are very well and very helpful to the world. Nevertheless, there are many people who need such devices lose their recognition in high frequency part, which may be caused by ageing auditory ossicles, ear drums or other auditory units.

When facing such cases, traditional hearing-aid devices do not help on provide complete audio information to people even they are turned on as loudly as they can, because there are some problems related to high frequency part of audio information not able to be received by ageing auditory parts of these people.

This may be a bigger and bigger problem in the future. Without high frequency information, users cannot enjoy music, causing some important parts are not recognized. In fact, even audio of daily conversation, when cutting its high frequency part, may be difficult to recognize, making people even with hearing-aid devices still find themselves difficult to 'hear' sounds sufficiently to have a normal life.

Therefore, there is a great need to develop a new product that can solve such problem, to make the world better.

SUMMARY OF INVENTION

The inventor invents various related hearing-aid devices to collect real audio information or created audio information and uses two sources to help people to 'hear'. First source is to use a speaker to generate a sound wave that may be via normal audio channel, i.e. the ear drum, the auditory ossicles, and the cochlear in sequence, or simply puts the speaker aside the round window to sends in sound wave in the inverse sequence order into the cochlear. When the speaker is placed aside, which means near, like between the eardrum and the round window, even a minor sound has great effect because the distance to auditory nerve cells are much closer than traditional path.

The second source is to place a needle, a soft band with multiple sub-electrodes, or any kind of electrical signal output device to directly or indirectly contact the auditory nerve cells by transmitting necessary electrical signal thereon. The auditory cell nerves near the round window is responsible for high frequency part. In addition, unlike traditional cochlear implant devices for people who cannot hear at all. The hearing-aid devices of the present invention mainly help people who can still hear when the sound is loud enough and particularly for those who have problem in high frequency audio processing.

The high frequency is compared to low frequency and middle frequency in different areas of the cochlear. It is experimented that one electrode is sufficient to provide certain high frequency information and helps combine a more complete audio recognition for those who originally lose the high frequency part. Please be noted that the prevent invention of course may be extended to provide more electrodes, even to the middle frequency part, or even be used with a complete cochlear implant.

There are various ways to implement the present invention, which means by adjusting some aspects of the concept mentioned above, a different device may be made for different needs. But, when they are based on providing both sound waves and electricity signals particularly to high frequency part, they are supposed to be covered by the present invention.

DETAILED DESCRIPTION

Part I. Illustrated Embodiments

According to an embodiment of the present invention, a hearing-aid apparatus has an audio collector, an audio processor, a speaker and an inner-ear implant device.

The audio collector may be one or more than one microphones, or any audio information generator or receivers for collecting audio information.

The speaker for generating a sound wave by reference to the audio information controlled by the audio processor. The sound wave is transmitted to an inner ear of a user.

The inner-ear implant device is to be implanted aside a round window of the user for generating an electrical signal controlled by the audio processor based on the audio information to stimulate high frequency auditory nerve cells of the user with an electrode of the inner-ear implant device.

The audio wave sent to the inner ear of the user and the electrical signal stimulating the auditory nerve cells of the user together form an integrated auditory recognition corresponding to the audio information.

Figure 1:
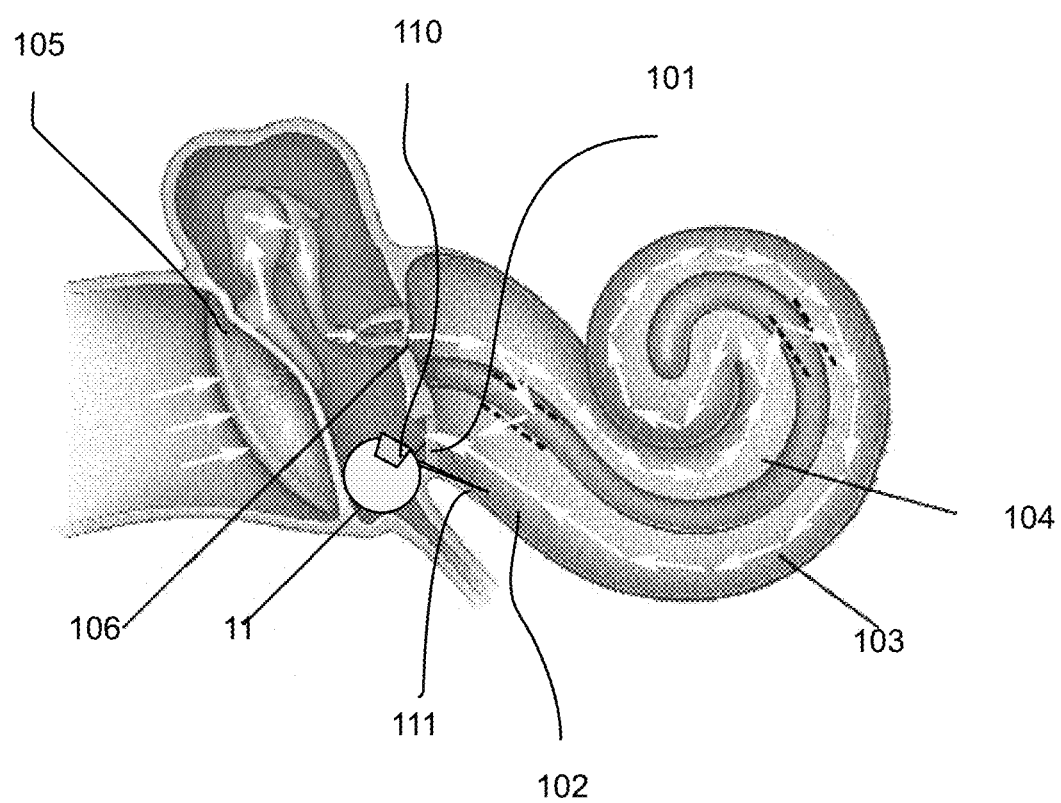
FIG. 1 illustrates a major part of an embodiment according to the present invention.

Please refer to FIG. 1, which illustrates an embodiment of the present invention.

In traditional sound transmission path, sound waves hit the eardrum 105 first, and the auditory ossicles amplify the sound and then cross the oval window 106, and then form a sound wave cross different positions, respectively responsible for low frequency part 104, middle frequency part 103 and high frequency part 102, of nerve cells in the cochlear. There is a round window 101 for releasing the air pressure of the sound wave in traditional path.

The hearing-aid device has an inner-ear implant device 11 with a speaker 110 to generates a sound wave routing in an inverted sequence, i.e. firstly entering the high frequency part 102, then the middle frequency part 103 and finally the low frequency part 104 of the cochlear.

In addition, the hearing-aid device has an electrode 111 to reach directly or indirectly to auditory nerve cells to stimulate the high frequency part 102 of the cochlear. The speaker 110 and the electrode 111 are controlled by a processor that can be integrated in the inner-ear implant received power from a battery, a wireless power transmission or a wire power transmission from an external device put on the external ear.

In some embodiments, the electrode 111 has a metal needle inserting through the skin so as to transmit corresponding current to the hearing nerve cells to generate hearing effect.

Some early experiments already show that the electrode generating a current to hearing nerve cells near the round window eliminate tinnitus. In other words, the hearing aid-device may be modified to keep only the electrode and corresponding current generator supplying currents to the electrode to generate stimulus to the hearing nerve cells near the round window, unlike traditional cochlear implant devices extending and spreading on most cochlear of an inner ear, to create a new product to cure tinnitus problems.

Such embodiment may be a tinnitus elimination apparatus comprising a current generator and an electrode. According to early experiments, the current generator generates a small current supplying to the electrode contacting the skin to transmit the small current to the hearing nerve near the round window. The small current is sufficient by using the current value used by traditional cochlear implant devices transmitting from its single electrode to eliminate tinnitus for a portion of patients.

Unlike traditional cochlear implant devices which needs to open a hole on skull to insert an elongated belt mounted with 16 or more electrodes spreading over the curved cochlear, the tinnitus elimination apparatus only needs a simple surgery without opening a hole on skull, which is explained with more details in following disclosure.

In other words, even those people without hearing problems, the tinnitus elimination device may also be used for solving tinnitus problems for a portion of patients.

Furthermore, for those patients with both tinnitus and hearing problems, the tinnitus elimination apparatus may be added with speakers, processors and other devices as mentioned above to be a hearing-aid apparatus which may be used to curing tinnitus problem at the same time.

Figure 3:
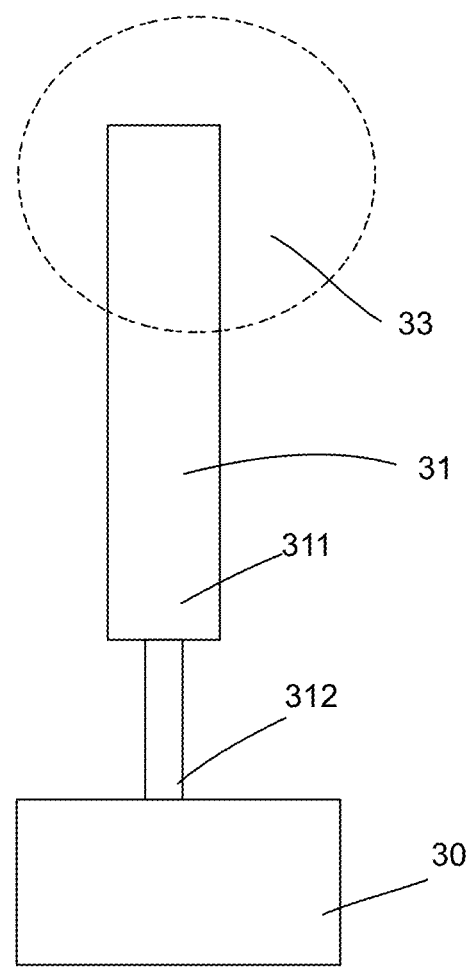
FIG. 3 illustrates an embodiment of an inner ear apparatus for curing tinnitus problem.

FIG. 3 shows an inner ear apparatus including a current circuit 30 and an electrode 31. The electrode 31 has a connector 312 and a contact electrode 311. The current circuit 30 generates a small current similar to a current for a single electrode of a traditional cochlear implant. The small current is sent to the contact electrode 311 via the connector 312. The connector 312 may be a wire wrapped with insulation layer or any conducting component for transmitting the small current to the contact electrode 311. The contact electrode 311 may include a needle to insert through a surface skin to stay contact with an inner ear area 33 aside to the round window of a user. The small current may be spread to stimulate some hearing nerve cells near the round window, which usually are processing high frequency portion. In some experiments, we find that such device cure tinnitus problems for a portion of patients.

The contact electrode 311 may be flexible. There may be a housing to wrap the current electrode. A battery may be integrated with the current circuit 30 or a wireless charging device may be used together to drive the current circuit 30 to generate the small current.

Figure 2:
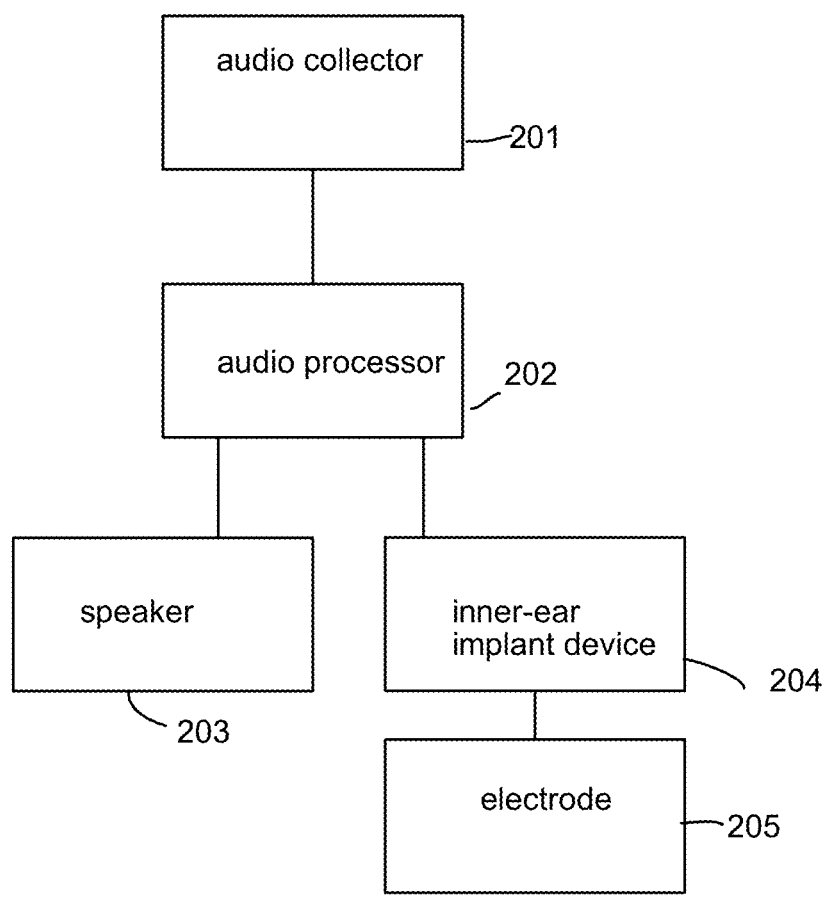
FIG. 2 is a diagram illustrating the architecture of an embodiment of a hearing-aid device.

FIG. 2 illustrates an architecture of the hearing-aid device embodiment, which may derive a lot of variations of products. As mentioned above, the hearing-aid device may also be used for eliminating tinnitus problem and thus may also be called inner hear apparatus, though not necessary all components are located insider an ear.

The audio collector 201 collects audio information. The audio processor 202 processes the audio information and controls the speaker 203 and the inner-ear implant device 204 that has an electrode 205 near the round window to generate sound wave and electricity signal for users to have a more complete audio recognition.

The audio collector can be a microphone or multiple microphones put on external ears or other places, e.g. a microphone array made as a necklace or from a phone as an auxiliary audio collector.

The processor may also be multiple separate parts, e.g. some part for power control and some part for encoding or wireless transmission.

In today's electronic technology, the processor may use a micro controller made of pure circuit logic to decrease power consumption and may also be implemented alternatively with a processor unit with one or multiple cores to execute stored programs. Configuration and programs may be stored in a logic table in a memory device. Other various implementation may also be done, e.g. several parts connected with wire and put at different positions in and/or out the ear.

In some embodiments, the speaker is integrated with the inner-ear implant device implanted aside the round window of the user. The speaker may be put in the ear canal connected with a microphone and related processor. As mentioned above, there are various ways to implement the inventions, depending on cost, user needs, user hearing cases, and even battery replacement consideration.

There are several wireless power transmission, particularly those used in human body, that may be used with the hearing-aid devices as mentioned here.

In some embodiments, the audio collector is a microphone put on an external ear for collecting environmental sounds as the audio information.

In some embodiment, the audio collector receives electronic sound data transmitted from an external device and converts the electronic sound data into the audio information.

In some embodiment, the electrode of the inner-ear plant device is a needle placed at high frequency portion of a cochlear of the user from the round window of the user to stimulate the auditory nerve cells.

In some embodiment, the electrode of the inner-ear implant device is a flexible band with a series of sub-electrodes to stimulate multiple positions of the high frequency potion of the cochlear.

In some embodiment, the electrode of the inner-ear implant device is a metal sheet, or any shapes that conducts electricity signal to auditory nerve cells from above skin or in the skin.

In some embodiments, the audio processor has an adjustable data list to be adjusted by an external device as a reference to convert the audio information to the electrical signal and the sound wave. Specifically, such adjustable data list may be a logic array in a memory device that may be changed conveniently.

In some embodiments, the external device is provided to a physician to operate with the external device to adjust stimulus strengths of the electronic signal and the sound wave. There may be also an external device or a mobile phone installed with an APP to implement such adjustment function, which may be controlled by users themselves for handling different needs in different situations.

In some embodiments, the adjustable data list is set and further adjusted by selecting one data group from candidate data groups, wherein the candidate data groups are collected and organized by collecting various users use-and-feedback data.

In some embodiments, in addition, there are more than one scenario data list to be selected and set to the adjustable data list. For example, audio information is very different for users on a bus or in a quiet room, also very different for users in a concert or in a conversation. Sometimes, the high frequency part may not be that necessary while the high frequency is critical and very meaningful, just try imagine what if Beethoven can hear better when he was old.

In some embodiments, the audio processor may automatically analyze the audio information and chooses one scenario data list to set as the adjustable data list. For example, the processor may analyze the collected information from the microphone.

In some embodiments, the scenario data lists comprise conversation scenario.

In some embodiments, the conversation scenario further comprises quiet place conversation scenario and noisy place conversation scenario.

In some embodiments, the scenario data lists comprise music scenario in which there is music playing involving high frequency information.

In some embodiments, the audio processor eliminates a high frequency portion of the audio information to generate the sound wave of the speaker and the high frequency portion of the audio information is converted to the electrical signal by the audio processor to stimulate the high frequency auditory nerve cells of the user.

In some embodiments, the audio processor keeps a high frequency portion of the audio information to generate the sound wave of the speaker and the high frequency portion of the audio information is converted to the electrical signal by the audio processor to stimulate the high frequency auditory nerve cells of the user.

In some embodiments, the audio processor comprises a portable part and a host part, the portable part is put on by the user all the time.

In some embodiments, the host part is a mobile phone running a corresponding app.

In some embodiments, the host part comprises a remote server connected via a network, e.g. for cloud computing with various A.I. (Artificial Intelligence) algorithms, like to perform instant language translation, emotion detection, etc.

In some embodiments, the processing of the audio information is partly handled by the portable part and partly handled by the host part. For example, a mobile phone or a specific mobile device may be used to enhance processor power and enrich or add various features, like language translation, audio correction based on multiple sources.

In some embodiments, the portable part of the audio processor handles routine hearing-aid mission of daily life of the user, and the host part enhances the audio information.

In some embodiments, when the host part handles at least some processing of the audio information.

In some embodiments, the host part generates the audio information. In other words, the audio information may be converted from a non-audio information, like computer vision to analyze a situation and converting into corresponding audio information, songs, or news.

The hearing-aid device may also have mobile phone function, if necessary wireless encoder and decoder are integrated while the audio output is converted into two sources, one source for soundwave and the other source for electricity signal stimulating auditory nerve cells.

In some embodiments, the audio processor detects audio commands to switch operation modes of the audio processor.

In some embodiments, the audio processor turns off the electrical signal when receiving an audio command.

In some embodiments, the audio processor detects a tap on an ear of the user to turn-off the electrical signal.

In some embodiments, the audio processor is connected with the electrode with a wireless signal.

In some embodiments, the audio processor is connected with the speaker with a wireless signal.

In some embodiments, the device further comprising an auxiliary microphone for collecting additional information of the audio information.

In some embodiments, the audio processor uses the additional information to determine and adjust the generated sound wave and the electrical signal corresponding to the audio information.

In some embodiments, there are multiple auxiliary microphones made as necklace shape device to be put on a neck of the user.

In some embodiments, the auxiliary microphone is put on a glass to be worn by the user.

To implant the above hearing-aid devices, the following method may be applied by a physician.

First, cut a skin of an ear canal of the user.

Roll up an ear drum of the user.

Place the inner-ear implant device as recited in any embodiments mentioned above.

Roll down the ear drum of the user.

Restore the cut skin of the ear canal.

Part II. Theory Explaining the Effectiveness, Enablement and Comparison with Past Devices As mentioned in the background, dated back to the first cochlear implant invented by Dr. William House in 1961, there are a lot of materials and matured products available to persons of ordinary skilled in the art of hearing devices, and the inventor believes these materials and products are sufficiently to explain and prove enablement that when an electrode is attached to auditory cells.

The electrical strength and patterns, not hurting human and provides effectiveness for human to generate audio recognition, can be found or measured in current products and related documents. But their developments focus on providing a full spectrum audio recognition to help people who cannot hear to hear.

That is different from the present invention, where the present invention helps particularly those who have problems in high frequency can 'hear' from two sources, one source from sound wave, vibration of air, and the other source from electrical signal stimulus.

Therefore, with the disclosure of this application, persons of ordinary skilled in the art certainly can create various embodiments based on the teaching of these disclosure. For example, cochlear implant manufacturers may cut most part of their electrode band but leave several high frequency bands with driving circuits and integrated with a hearing-aid device that can generate sound waves.

As mentioned above, there are various ways to implement the present invention, depending on different cost concerns or patient requirements. The electrode of the implant device may even be disabled at first time or even not provided but only added when necessary, e.g. when ageing people start losing their hearing on high frequency audio information.

Therefore, applicant believes the disclosure is sufficient and meets enablement and written description, novelty and nonobviousness requirements of the patent law.

There are various aspects for implementing the hearing-aid apparatus and they are summarized by structure outlines as follows.

1. A hearing-aid apparatus, comprising:
    an audio collector, for collecting audio information;
    an audio processor;
    a speaker for generating a sound wave by reference to the audio information controlled by the audio processor, wherein the sound wave is transmitted to an inner ear of a user; and
    an inner-ear implant device to be implanted aside a round window of the user for generating an electrical signal controlled by the audio processor based on the audio information to stimulate high frequency auditory nerve cells of the user with an electrode of the inner-ear implant device, wherein
    the audio wave sent to the inner ear of the user and the electrical signal stimulating the auditory nerve cells of the user together form an integrated auditory recognition corresponding to the audio information.

2. The hearing-aid apparatus of item 1, wherein the speaker is integrated with the inner-ear implant device implanted aside the round window of the user.

3. The hearing-aid apparatus of item 1, wherein the audio collector is a microphone put on an external ear for collecting environmental sounds as the audio information.

4. The hearing-aid apparatus of item 1, wherein the audio collector receives electronic sound data transmitted from an external device and converts the electronic sound data into the audio information.

5. The hearing-aid apparatus of item 1, wherein the electrode of the inner-ear plant device is a needle placed at high frequency portion of a cochlear of the user from the round window of the user to stimulate the auditory nerve cells.

6. The hearing-aid apparatus of item 1, wherein the electrode of the inner-ear implant device is a flexible band with a series of sub-electrodes to stimulate multiple positions of the high frequency potion of the cochlear.

7. The hearing-aid apparatus of item 1, wherein the electrode of the inner-ear implant device is a metal sheet.

8. The hearing-aid apparatus of item 1, wherein the audio processor has an adjustable data list to be adjusted by an external device as a reference to convert the audio information to the electrical signal and the sound wave.

9. The hearing-aid apparatus of item 8, wherein the external device is provided to a physician to operate with the external device to adjust stimulus strengths of the electronic signal and the sound wave.

10. The hearing-aid apparatus of item 8, wherein the adjustable data list is set and further adjusted by selecting one data group from candidate data groups, wherein the candidate data groups are collected and organized by collecting various users use-and-feedback data.

11. The hearing-aid apparatus of item 8, wherein there are more than one scenario data list to be selected and set to the adjustable data list.

12. The hearing-aid apparatus of item 11, wherein the audio processor automatically analyzes the audio information and chooses one scenario data list to set as the adjustable data list.

13. The hearing-aid apparatus of item 11, wherein the scenario data lists comprise conversation scenario.

14. The hearing-aid apparatus of item 13, wherein the conversation scenario further comprises quiet place conversation scenario and noisy place conversation scenario.

15. The hearing-aid apparatus of item 11, wherein the scenario data lists comprise music scenario in which there is music playing involving high frequency information.

16. The hearing-aid apparatus of item 1, wherein the audio processor eliminates a high frequency portion of the audio information to generate the sound wave of the speaker and the high frequency portion of the audio information is converted to the electrical signal by the audio processor to stimulate the high frequency auditory nerve cells of the user.

17. The hearing-aid apparatus of item 1, wherein the audio processor keeps a high frequency portion of the audio information to generate the sound wave of the speaker and the high frequency portion of the audio information is converted to the electrical signal by the audio processor to stimulate the high frequency auditory nerve cells of the user.

18. The hearing-aid apparatus of item 1, wherein the audio processor comprises a portable part and a host part, the portable part is put on by the user all the time.

19. The hearing-aid apparatus of item 18, wherein the host part is a mobile phone running a corresponding app.

20. The hearing-aid apparatus of item 18, wherein the host part comprises a remote server connected via a network.

21. The hearing-aid apparatus of item 18, wherein the processing of the audio information is partly handled by the portable part and partly handled by the host part.

22. The hearing-aid apparatus of item 18, wherein the portable part of the audio processor handles routine hearing-aid mission of daily life of the user, and the host part enhances the audio information.

23. The hearing-aid apparatus of item 18, wherein when the host part handles at least some processing of the audio information.

24. The hearing-aid apparatus of item 18, wherein the host part generates the audio information.

25. The hearing-aid apparatus of item 24, wherein the host part generates the audio information based on non-audio information.

26. The hearing-aid apparatus of item 1, wherein the audio processor detects audio commands to switch operation modes of the audio processor.

27. The hearing-aid apparatus of item 26, wherein the audio processor turns off the electrical signal when receiving an audio command.

28. The hearing-aid apparatus of item 1, wherein the audio processor detects a tap on an ear of the user to turn-off the electrical signal.

29. The hearing-aid apparatus of item 1, wherein the audio processor is connected with the electrode with a wireless signal.

30. The hearing-aid apparatus of item 1, wherein the audio processor is connected with the speaker with a wireless signal.

31. The hearing-aid apparatus of item 1, further comprising an auxiliary microphone for collecting additional information of the audio information.

32. The hearing-aid apparatus of item 31, wherein the audio processor uses the additional information to determine and adjust the generated sound wave and the electrical signal corresponding to the audio information.

33. The hearing-aid apparatus of item 31, wherein there are multiple auxiliary microphones made as necklace shape device to be put on a neck of the user.

34. The hearing-aid apparatus of item 31, wherein the auxiliary microphone is put on a glass to be worn by the user.

35. A method for implanting an implant component of a hearing-aid device in a user, comprising:
cutting a skin of an ear canal of the user;
rolling up an ear drum of the user;
placing the inner-ear implant device as recited in any of claim 1 to claim 34;
rolling down the ear drum of the user; and
restoring the cut skin of the ear canal.

The invention claimed is:

1. An inner ear apparatus, comprising:
an audio collector, for collecting audio information;
an audio processor;
a speaker for generating a sound wave by reference to the audio information controlled by the audio processor, wherein the sound wave is transmitted to an inner ear of a user; and
an inner-ear implant device being configured to be implanted aside a round window of the user for generating an electrical signal controlled by the audio processor based on the audio information to stimulate high frequency auditory nerve cells of the user with an electrode of the inner-ear implant device, wherein
the audio wave sent to the inner ear of the user and the electrical signal stimulating the auditory nerve cells of the user together form an integrated auditory recognition corresponding to the audio information, wherein the speaker is integrated with the inner-ear implant device implanted, wherein the integrated speaker and the inner-ear implant are configured to be together placed aside the round window and inside the eardrum of the user.

2. The inner ear apparatus of claim 1, wherein the speaker is integrated with the inner-ear implant device implanted aside the round window of the user.

3. The inner ear apparatus of claim 1, wherein the audio collector is a microphone configured to be put on an external ear for collecting environmental sounds as the audio information.

4. The inner ear apparatus of claim 1, wherein the audio collector receives electronic sound data transmitted from an external device and converts the electronic sound data into the audio information.

5. The inner ear apparatus of claim 1, wherein the electrode of the inner-ear plant device is a needle configured to be placed at high frequency portion of a cochlear of the user from the round window of the user to stimulate the auditory nerve cells.

6. The inner ear apparatus of claim 1, wherein the electrode of the inner-ear implant device is a flexible band with a series of sub-electrodes to stimulate multiple positions of the high frequency potion of the cochlear.

7. The inner ear apparatus of claim 1, wherein the electrode of the inner-ear implant device is a metal sheet.

8. The inner ear apparatus of claim 1, wherein the audio processor has an adjustable data list to be adjusted by an external device as a reference to convert the audio information to the electrical signal and the sound wave.

9. The inner ear apparatus of claim 8, wherein the external device is provided to a physician to operate with the external device to adjust stimulus strengths of the electronic signal and the sound wave.

10. The inner ear apparatus of claim 9, wherein the adjustable data list is set and further adjusted by selecting one data group from candidate data groups, wherein the candidate data groups are collected and organized by collecting various users use-and-feedback data.

11. The inner ear apparatus of claim 9, wherein there are more than one scenario data list to be selected and set to the adjustable data list.

12. The inner ear apparatus of claim 11, wherein the audio processor automatically analyzes the audio information and chooses one scenario data list to set as the adjustable data list.

13. The inner ear apparatus of claim 11, wherein the scenario data lists comprise conversation scenario.

14. The inner ear apparatus of claim 13, wherein the conversation scenario further comprises quiet place conversation scenario and noisy place conversation scenario.

15. The inner ear apparatus of claim 11, wherein the scenario data lists comprise music scenario in which there is music playing involving high frequency information.

16. The inner ear apparatus of claim 1, wherein the audio processor eliminates a high frequency portion of the audio information to generate the sound wave of the speaker and the high frequency portion of the audio information is converted to the electrical signal by the audio processor to stimulate the high frequency auditory nerve cells of the user.

17. The inner ear apparatus of claim 1, wherein the audio processor keeps a high frequency portion of the audio information to generate the sound wave of the speaker and the high frequency portion of the audio information is converted to the electrical signal by the audio processor to stimulate the high frequency auditory nerve cells of the user.

18. The inner ear apparatus of claim 1, wherein the audio processor comprises a portable part and a host part, the portable part is configured to be put on by the user all the time.

\* \* \* \* \*